United States Patent [19]
Maxted et al.

[11] Patent Number: 5,342,411
[45] Date of Patent: Aug. 30, 1994

[54] SCALP COOLING DEVICE

[75] Inventors: Kenneth J. Maxted, Glasgow, Scotland; Neville Mountford, Lincoln, England

[73] Assignee: Greater Glasgow Health Board, Glasgow, Scotland

[21] Appl. No.: 17,344

[22] Filed: Feb. 2, 1993

Related U.S. Application Data

[63] Continuation of Ser. No. 585,076, Nov. 14, 1990, abandoned.

[30] Foreign Application Priority Data

Apr. 16, 1988 [GB] United Kingdom ............ 8809029.5

[51] Int. Cl.$^5$ .................................................. A61F 7/00
[52] U.S. Cl. ...................................... 607/107; 607/110
[58] Field of Search ........................... 128/399–403, 128/379, 380; 62/272, 285, 412, 516; 165/66, 62; 607/107, 110

[56] References Cited

U.S. PATENT DOCUMENTS

| | | |
|---|---|---|
| 1,846,312 | 2/1932 | Loghlan . |
| 2,247,406 | 7/1941 | Rudolph . |
| 2,463,090 | 3/1949 | Dixon et al. ............ 62/285 |
| 2,817,340 | 12/1957 | Cuvier . |
| 2,875,486 | 5/1959 | Holm .................... 165/66 |
| 3,307,553 | 3/1967 | Liebner . |
| 3,587,577 | 6/1971 | Smirnov et al. . |
| 3,866,612 | 2/1975 | Buker . |
| 3,908,655 | 9/1975 | Lund . |
| 3,963,466 | 6/1976 | Hynes ................... 62/272 |
| 4,193,443 | 3/1980 | Nanaumi et al. ........ 62/272 |
| 4,196,630 | 4/1980 | Rudolph ............. 128/660.01 |
| 4,235,081 | 11/1980 | Dowling ................ 62/272 |
| 4,572,188 | 2/1986 | Augustine et al. . |

FOREIGN PATENT DOCUMENTS

| | | |
|---|---|---|
| 76080 | 4/1983 | European Pat. Off. . |
| 2247406 | 4/1974 | Fed. Rep. of Germany . |
| 2195421 | 3/1974 | France . |
| 302120 | 4/1971 | U.S.S.R. . |
| 0076080 | 4/1983 | United Kingdom . |
| 82/04184 | 12/1982 | World Int. Prop. O. . |

*Primary Examiner*—Mark S. Graham
*Attorney, Agent, or Firm*—Pennie & Edmonds

[57] ABSTRACT

Scalp cooling apparatus is described in which an air flow is recirculated so as to reduce entrained moisture to that initially in the air circuit and to the direct contribution of moisture resulting from evaporation from the scalp, and by matching the impedance between the delivery tubing and evaporation orifice for warm incoming air and chilled outgoing air. In one arrangement an applicator helmet has an air delivery gallery which directs air onto the scalp and hairline through a number of profile drillings of such size and profile as to minimize frictional losses in the air stream. Air is extracted at the crown of the helmet where the convergence and increasing air velocity compensates for increased air temperature so that at this point, scalp cooling is optimized by using the wind-chill effect. The interior of the helmet includes a number of spacers which are held in gentle contact with the scalp by applying a slight force in the helmet using a counter-balanced arm. This permits the helmet to remain in contact with the scalp even as the patient relaxes and slumps in the chair during treatment. The helmet is also provided with an elasticated fabric skirt to reduce air loss from the closed air recirculation circuit.

8 Claims, 2 Drawing Sheets

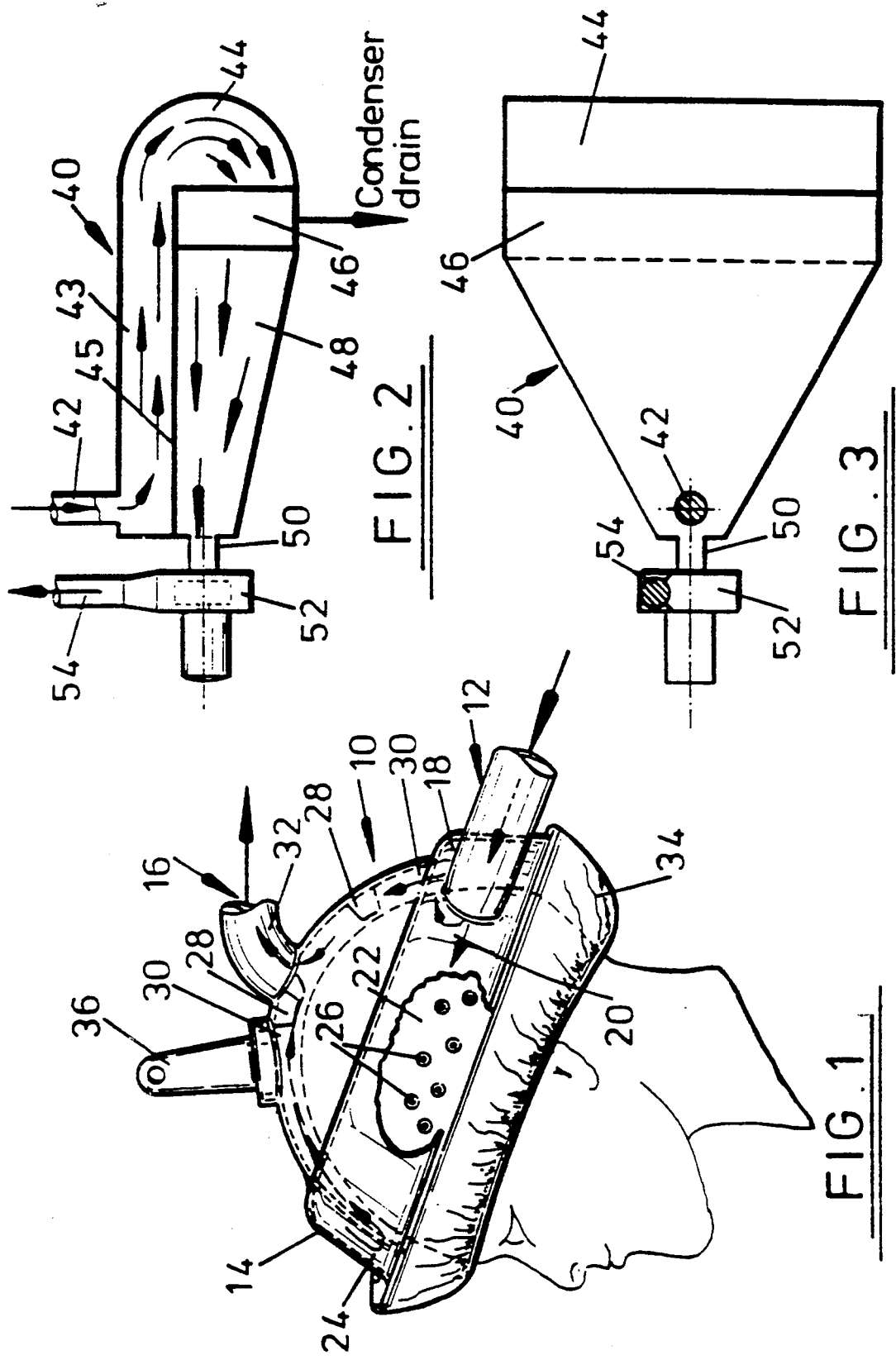

SCALP COOLING DEVICE

This is a continuation, of application Ser. No. 07/585,076, filed Nov. 14, 1990, now abandoned.

FIELD OF THE INVENTION

The present invention relates to a cooling apparatus and especially, but not exclusively, to scalp cooling apparatus and to a method of cooling a scalp which is particularly suitable for treating patients undergoing chemotherapy.

BACKGROUND OF THE INVENTION

The use of cytotoxic agents in, for example, chemotherapy of cancer patients almost inevitably causes hair loss known as alopecia. Alopecia can be prevented by cooling the scalp because drug uptake by hair follicles is reduced as a consequence of cutaneous vasoconstriction and the inhibition of cellular metabolic pathways. Cooling can be achieved in a number of ways: by circulating chilled liquid in close thermal contact with the scalp; by the application of crushed ice packs or shaped cryogel packs; by the activation of endothermic chemical reactions, and by the circulation of cold air over the scalp.

Cold air scalp cooling has several advantages over the other cooling methods. Firstly it requires no additional thermal contact medium thus, unlike all the other methods, hair wetting is not required. The technique can be applied with very little weight being imposed on the patients head and is therefore much less tiring and uncomfortable, and thermal transfer can be optimised over the entire scalp by design of the applicator helmet.

Clinical trials have been performed using a vortex tube air refrigerator as described in the paper entitled "Adriamycin Alopecia Prevented by Cold Air Scalp Cooling" published in American Journal of Clinical Oncology (CCT) 9(5):454–457, 1986 by Symonds McCormick and Maxted. This disclosure established the requirements for temperature and air flow and demonstrated that clinical results, equalling or exceeding any previously published, could be achieved without skill of application or degree of preparation required for any of the other methods.

However the use of standard refrigeration components to provide a source of cold air has a number of problems. Namely freezing of entrained moisture on the evaporator causes low efficiency due to latent heat loses and airflow obstruction and the circulating fan causes significant heat gain. The helmet and tubing design described in the above paper did not permit sufficient free flow of air to avoid significant pressure drops.

SUMMARY OF THE INVENTION

An object of the present invention is to provide an improved cooling system which obviates or mitigates at least one of the aforesaid disadvantages.

This is achieved by recirculating the air flow so as to reduce entrained moisture to that initially in the air circuit and to the direct contribution of moisture resulting from evaporation from the scalp, and by matching the impedance between the delivery tubing and evaporation orifice for warm incoming air and chilled outgoing air.

In a preferred arrangement an applicator helmet has an air delivery gallery which directs air onto the scalp and hairline through a number of profile drillings of such size and profile as to minimize frictional loses in the air stream. Air is extracted at the crown of the helmet where the convergance and increasing air velocity compensates for increased air temperature so that at this point, scalp cooling is optimised by using the wind-chill effect. The interior of the helmet includes a number of spacers which are held in gentle contact with the scalp by applying a slight force in the helmet using a counterbalanced arm. This permits the helmet to remain in contact with the scalp even as the patients relaxes and slumps in the chair during treatment. The helmet is also provided with an elasticated fabric skirt to reduce air loss from the closed air recirculation circuit.

According to one aspect of the present invention there is provided a helmet for use with a recirculating scalp cooling system, said helmet comprising air inlet means and air outlet means, said air inlet means being provided by a plurality of apertures disposed around the periphery of the rim of the helmet, said air outlet means being disposed at the crown of said helmet, and spacing means located inside the helmet for setting the distance between the helmet and the scalp.

Conveniently the helmet is of a partial double skin construction with the air inlet means including a plurality of apertures disposed around the periphery of the inner skin.

Preferably an elasticated skirt is coupled to the rim of the helmet to minimise air loss from the helmet and/or to prevent entrainment of room air into the helmet.

Preferably the spacing means is provided by projections fastened to the interior surface of the helmet, said projections being of a predetermined size so as to define an acceptable gap between the scalp and the helmet to permit air to flow there through. Alternatively said projections are adjustable relative to interior surfaces of helmet to permit the gap between the helmet and the scalp to be varied.

Conveniently the top of helmet includes force coupling means by which a force can be applied to the helmet to maintain the helmet in constant contact with the scalp during treatment of the patient. Conveniently the coupling means is a projection disposed near the crown of the helmet.

According to another aspect of the present invention there is provided scalp cooling apparatus comprising cooling means for cooling a volume of air, fan means for supplying said cooled volume of air to a helmet adapted to be fitted over a subject, said helmet being adapted to deliver said cooled air to the scalp of said subject, said helmet having an air outlet for receiving air warmed by the scalp, chamber means for recirculating the warmed air from such scalp through said cooling means, means coupled to the chamber means for reducing the moisture content entrained in said air flow, said fan means recirculating cooled air through said helmet.

Preferably said cooling means comprises an evaporator, a compressor and an expansion valve in a refrigeration circuit.

Preferably the evaporator is disposed in a said chamber means, said chamber means having an input plenum for receiving air warmed by the scalp, and which gradually increases in size from its inlet to the evaporator and an output plenum which decreases in size from the evaporator to a cool air outlet.

Preferably said input plenum includes a plurality of vanes coupled to the evaporator to distribute air flow over said evaporator surface, and said evaporator is coupled to a condensate drain.

Preferably also said fan means is a centrifugal fan disposed at said output plenum chamber cool air outlet or alternatively at said input plenum warm air input for supplying cooled air with a reduced moisture content to said helmet inlet means.

Preferably also said scalp cooling apparatus includes means for maintaining the helmet in gentle contact with the scalp. Conveniently said contact means are provided by a counterbalance arm having one end coupled to helmet and the other end coupled to counterweight. Alternatively said means of maintaining the helmet in contact with the scalp may be provided by coil springs or constant tension springs.

According to another aspect of the present invention there is provided a method of supplying cooled air to the scalp of a subject, said method comprising the steps of; cooling a predetermined volume of air to a predetermined temperature range; supplying cooled air within said predetermined temperature range to a helmet adapted to receive a scalp for being cooled; removing air heated by said scalp from said helmet; reducing the moisture content of said air and recooling said air; and recirculating said cooled air back through said helmet.

Conveniently said method also comprises the step of matching the impedance between the delivery tubing receiving air heated by said scalp and the evaporation orifice through which chilled outgoing air is emitted to be recirculated through said helmet. Conveniently also said method also comprises the step of optimising scalp cooling by using the wind chill effect.

According to another aspect of the invention there is provided cooling apparatus for cooling a portion of a body comprising cooling means for cooling a volume of air, fan means for supplying said cooled volume of air to a delivery means adapted to be fitted over part of the body of a subject, said delivery means being adapted to deliver said cooled air to the body part of said subject, said delivery means having an air outlet for receiving air warmed by the body part, chamber means for recirculating the warmed air from such body part through said cooling means, evaporation means coupled to the chamber means for reducing the moisture content entrained in said air flow, said fan means recirculating cooled air through said delivery means, said chamber means including a plenum assembly having an inlet plenum with an assembly inlet for receiving gas to be cooled and dried, an outlet plenum for delivering cooled dried gas to an assembly outlet, and plate means separating the inlet and outlet plenum, said evaporation means being disposed between said inlet and outlet plenum.

Preferably said plenum assembly and said separate plate are generally horizontally disposed. Alternatively said plenum assembly and said separate plate is vertically disposed and said evaporator is disposed at the lowermost between said inlet and outlet plenums. Conveniently said part of the body is the scalp and said delivery means is a helmet.

BRIEF DESCRIPTION OF THE DRAWINGS

These and other aspects of the invention will become apparent from the following description when taken in combination with the accompanying drawings which:

FIG. 1 is a diagrammatic view of a helmet in accordance with an embodiment of one aspect of the invention shown mounted on the head of a subject;

FIG. 2 is a diagrammatic sectional view of a plenum chamber for receiving air warmed by the scalp for reducing moisture content and for recirculating cooled air back to said scalp in accordance with an embodiment of another aspect of the present invention;

FIG. 3 is a top plan view of a receiving chamber shown in FIG. 2; and

DETAILED DESCRIPTION OF THE DRAWINGS

Figure 4:
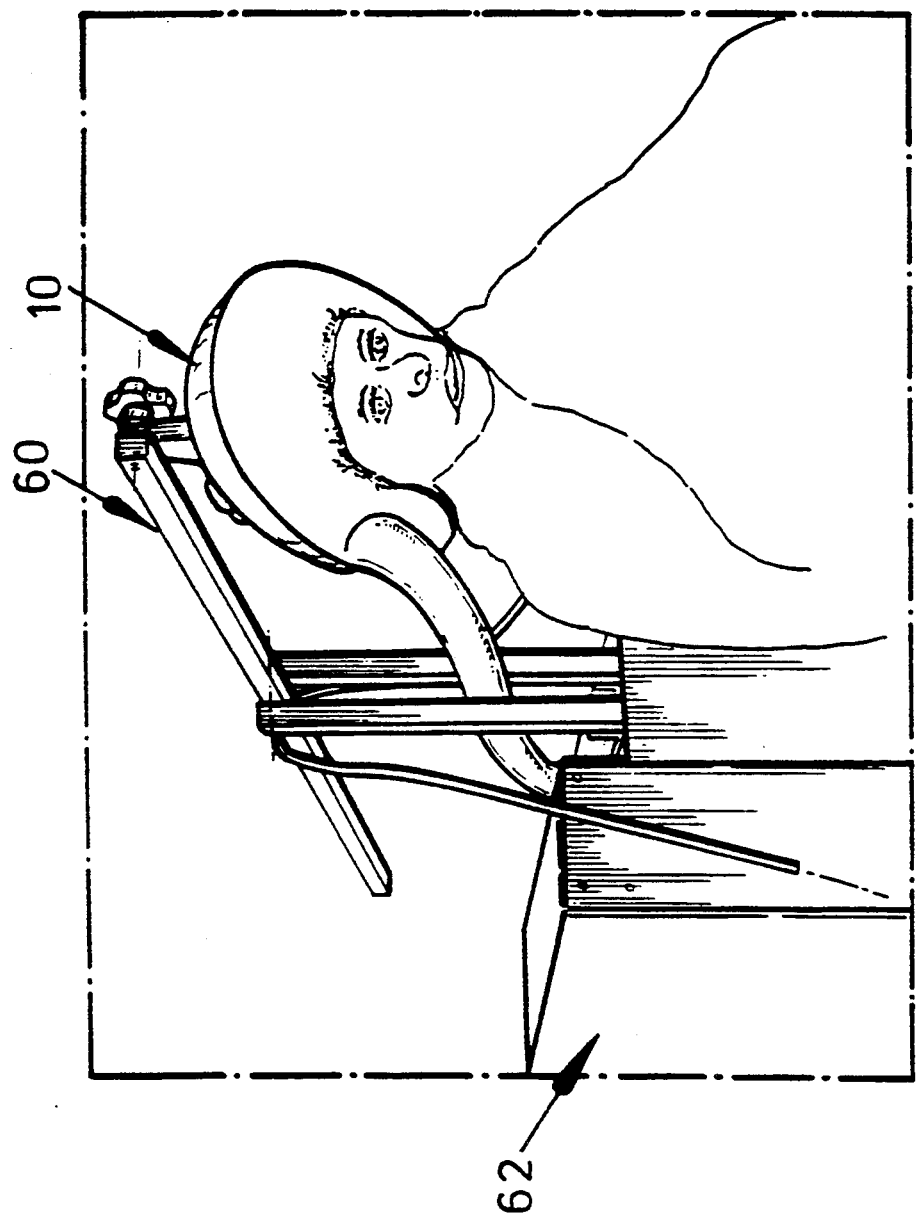
FIG. 4 is a photograph of an embodiment of the invention shown in use on a patient.

Reference is first made to FIG. 1 of the drawings which depicts a helmet generally indicated by the reference numeral 10 which is shown fitted on the head of a patent and which has an inlet 12 for receiving chilled air for cooling the scalp disposed at the rim 14 of the helmet and an air outlet 16 for returning air warmed by the scalp to a refrigeration unit for further cooling and reduction of moisture content as will be later explained in detail.

The helmet 10 is vacuum formed from plastic and is of a partial double skin construction in the vicinity of the rim 14. A flexible air inlet pipe or conduit 18 is coupled to the outer helmet skin 20 and air is supplied into a cavity 24 disposed between the inner and outer skins 22 and 20. Disposed around the periphery of the inner skin 22 are two rows of 6 mm diameter apertures 26 which are dimensioned and chamfered so as to minimize frictional losses in the air stream. Thus air supplied at the inlet 12 through conduit 18 is fed around the periphery of the rim 14 between the inner and outer skins 20, 22 and through apertures 26 and onto the scalp in the vicinity of the hair line.

The interior helmet skin 22 is spaced from the scalp by a plurality of rubber projections 28 to define a gap 30 between the helmet and the scalp to permit cool air fed through the apertures 26 to circulate over the scalp. Alternatively, the projections are adjustable relative to interior surfaces of the helmet to permit the gap between the helmet and the scalp to be varied.

Air circulating over the scalp is extracted at the crown of the helmet by flexible outlet conduit 32 which passes through the single helmet skin at the crown.

The rim of the helmet 14 has an elasticated fabric skirt 34 depending therefrom for sealing the helmet around the head of the subject. The fabric skirt restricts the entrainment of room air into the system and improves cooling air flow at the hair line margin. The fabric skirt also minimises any air loss from the closed circuit.

Near the crown of the helmet is coupled an upstanding projection 36 to which a counterbalance arm can be connected (as best seen in FIG. 4) for holding the helmet 10 in gentle contact with the scalp during treatment as will be later described in detail.

Reference is now made to FIGS. 2 and 3 of the drawings which depicts a plenum assembly, generally indicated by a reference numeral 40, for receiving air warmed by the scalp and for reducing moisture content of the air and for recirculating cooled drier air to the helmet 10. The plenum assembly 40 has an inlet conduit 42 which is coupled to conduit 32 for receiving air warmed by the scalp. The inlet 42 feeds into an input plenum 43 which diverges from inlet 42 for guiding the warmed air over a plurality of air vanes 44 and then onto an evaporator indicated by reference numeral 46 which is a coil element from a 550 watt Searle TF2-0.3 cooler unit. The evaporator is coupled to a condensate drain from which condensed moisture can be removed.

The evaporator is also coupled to an output plenum 48 which converges towards an output plenum output 50. The output plenum is in thermal contact with the input plenum via separating plate 45. At the outlet 50 is coupled a single inlet centrifugal fan 52 of the free air type VBM4, Air Control Installation Limited and which has a free air supply of 76 cubic feet per minute. A fan outlet 54 is coupled to a conduit which supplies cooled drier air to the inlet conduit 18 coupled to the helmet 10.

It will be appreciated that both the input plenum 43 and the output plenum 48 are tapered or wedge-shaped so that initially the warm air flows through air inlet 42 and then diverges and flows over the separating plate 45 towards the full evaporator width 46. The plate 45 removes some moisture as does the evaporator 46 and chilled air from the evaporator then converges towards the plenum outlet 50. The tapered plenum design of both the input and the output plenums 43, 48 provides an impedance match between the delivery tubing 42, 54 and the evaporator orifice for both warm incoming air so that kinetic energy losses are minimised. Thus a sufficient volume of air can be recirculated through the closed system by the fan 54.

The plenum chamber 40 is part of the refrigeration circuit which includes a fridge compressor and an automatic expansion valve, which are standard commercial components for room air chillers whose construction is in accordance with established techniques.

Reference is now made to the photograph shown in FIG. 4 of the drawings which depicts cooling apparatus in use on a patient. It will be seen that the helmet 10 is maintained in position by the counterbalanced arm 60 while the patient is seated in the chair. Flexible conduits connects the helmet 10 to the refrigeration unit, generally indicated by reference numeral 62, which includes the standard refrigeration components such as the compressor, evaporator, expansion valve centrifugal fan and condensate drain and some electrical switches.

In operation, the helmet 10 is disposed on a patient and the system is switched on so that the scalp is pre-cooled for around 10 minutes. Then drug infusion is performed for about 5 minutes and the patient then undergoes a period of treatment typically half an hour, because in this period the liver reduces the activity of the infused drug. The amount of pre-cooling, drug infusion, and post-cooling will vary from patient to patient and will depend on specific drugs however these figures are exemplary of a typical treatment regime.

When the system is switched on the air helmet directs cool air onto the scalp at the hair line through the apertures 26. The air then flows in the direction of the arrows shown in FIG. 1 over the scalp and out through outlet 16 back to the air recirculating plenum assembly 40. Because air is extracted at the crown of the helmet the convergence and increasing air velocity compensates for increased air temperature at this point due to heat being extracted from the scalp and thus scalp is optimised by using the wind-chill effect.

It will be appreciated that no control unit is required because, under normal ambient temperature conditions, the rate of heat flow from the air circulation circuit is limited by evaporator size and by the refrigerant used which can be any suitable refrigerant such as ammonia, ethyl chloride or Freon (trademark). With the system disclosed the air delivery between 11–27 cubic feet per minute at 0° C. and operational back pressures is obtained, and it has been found that the air delivery temperature at the helmet orifice is between −7° C.– 3° C. The exhaust temperature at the helmet crown has been measured at about +3° C. With the apparatus herein before described the cooling capacity was assessed by the use of a dummy scalp with uniform power dissipation in the form of a buried heated wire network and has been found to be 30 watts at 18° C. scalp temperature and 18 watts at 14° C. scalp temperature. It will also be appreciated under normal conditions of use the apparatus requires no defrosting cycle.

Various modifications may be made to the helmet and scalp cooling apparatus hereinbefore described without departing from the scope of the invention. For example the elasticated skirt may be omitted and the helmet may be maintained in position by means of coil springs or tensator springs instead of using counterbalance weights. The gap spacers inside the helmet can be rubber or plastic or any other suitable material which can greatly contact the scalp which will permit a suitable flow of chilled air over the scalp during use. It will also be appreciated that although a compression refrigerator is described herein an absorption refrigerator without the compressor could be used instead in accordance with established technology. In addition the size and shape of the apertures 26 in the inner helmet skin may be varied as required to optimize air supply in cooling and the air outlet can be taken from a single or multiple point consistent with obtaining fixed scalp cooling. It will also be understood that the system could be used to supply air within a predetermined temperature range to other body sites for cooling such as the hands or feet. The plenum assembly could be disposed vertically so that the separating plate is vertical and the evaporator is located at the lowermost position between the plenum to facilitate condensation and moisture removal. An equivalent gas to air or air mixture could also be used with this apparatus.

Advantages of the system are that the helmet design is suitable for use with the majority of adult head sizes and does not require any adjustment except for the positioning of an elasticated fabric skirt at the periphery for restricting the entrainment of room air into the system and for improving cooling air flow at the hair line margin. The system does not require the use of control units even a thermostat and under normal conditions of use the unit requires no defrosting cycle. In addition the system is capable of continuous running and requires minimal maintenance. The problem of freezing of entrained moisture on the evaporator is obviated, the circulating fan does not result in significant heat gain and the volume of air delivery is sufficient to cause satisfactory cooling of the scalp.

We claim:

1. A helmet for use with a recirculating air scalp cooling system, said helmet arranged for location over the scalp of a patient and defining a rim, a crown, air inlet means and air outlet means, said air inlet means being provided by a plurality of apertures disposed around said rim of the helmet, said air outlet means being disposed at said crown of the helmet, and spacing means comprising interior projections located inside the helmet for setting the distance between the helmet and the scalp to permit air to flow therebetween, wherein said projections are adjustable to permit the gap between the helmet and the scalp to be varied.

2. Scalp cooling apparatus comprising:
   (a) a helmet arranged to be fitted over the scalp of a subject defining air inlet means and air outlet means and for defining an air passage between the helmet and the scalp between said air inlet means and said air outlet means;
(b) cooling means for cooling a volume of air;
(c) fan means for supplying said cooled volume of air to said helmet air inlet means;
(d) chamber means for receiving warmed air from said helmet air outlet means and recirculating air through said cooling means;
(e) means coupled to the chamber means for reducing the moisture content entrained in said air prior to said warmed air being recirculated through said cooling means; and
(f) biasing means external to the helmet for biasing the helmet into gentle contact with the scalp during patient movements.

3. Scalp cooling apparatus as claimed in claim 2 wherein said cooling means comprises an evaporator, a compressor and an expansion valve in a refrigeration circuit.

4. Scalp cooling apparatus as claimed in claim 3 wherein the evaporator is disposed in said chamber means, said chamber means having an input plenum for receiving air warmed by the scalp, and which gradually increases in cross section from an inlet to the evaporator and an output plenum which decreases in cross section from the evaporator to a cool air outlet.

5. Scalp cooling apparatus as claimed in claim 4 wherein said input plenum includes a plurality of vanes coupled to the evaporator to distribute air flow over a surface of the evaporator, and said evaporator is coupled to a condensate drain.

6. Scalp cooling apparatus as claimed in claim 4 wherein said fan means is a centrifugal fan disposed at said output plenum chamber cool air outlet or alternatively at said input plenum warm air inlet for supplying cooled air with a reduced moisture content to said helmet air inlet means.

7. Scalp cooling apparatus as claimed in claim 2 wherein said biasing means are provided by a counterbalance arm having one end coupled to said helmet and the other end coupled to a counterweight.

8. Scalp cooling apparatus as claimed in claim 2 wherein said biasing means are provided by coil springs or constant tension springs.

* * * * *